(12) United States Patent
Plicchi et al.

(10) Patent No.: US 6,318,375 B1
(45) Date of Patent: Nov. 20, 2001

(54) DEVICE FOR LOCATING ENDOCARDIAL ELECTRODES

(75) Inventors: Gianni Plicchi, Bologna; Bruno Garberoglio, Turin; Guido Gaggini, Milan; Franco Vallana, Turin; Emanuela Marcelli, Macerata, all of (IT)

(73) Assignee: Ministero dell' Universita' e della Ricera Scientifica e Tecnologica, Rome (IT)

( * ) Notice: Subject to any disclaimer, the term of this patent is extended or adjusted under 35 U.S.C. 154(b) by 0 days.

(21) Appl. No.: 09/301,183

(22) Filed: Apr. 28, 1999

(30) Foreign Application Priority Data

Jan. 28, 1999 (EP) .................................. 99830032

(51) Int. Cl.[7] .................................................. A61B 19/00
(52) U.S. Cl. ............................................................. 128/899
(58) Field of Search .................................. 600/424, 374, 600/509; 128/899

(56) References Cited

U.S. PATENT DOCUMENTS

| | | | |
|---|---|---|---|
| 5,297,549 | * | 3/1994 | Beatty et al. ........................ 600/374 |
| 5,553,611 | * | 9/1996 | Budd et al. .......................... 600/374 |
| 5,662,108 | * | 9/1997 | Budd et al. .......................... 600/374 |
| 5,752,513 | * | 5/1998 | Acker et al. ......................... 600/424 |
| 5,855,592 | * | 1/1999 | McGee et al. ....................... 600/374 |
| 5,876,336 | * | 3/1999 | Swanson et al. .................... 600/374 |
| 5,899,860 | * | 5/1999 | Pfeiffer et al. ...................... 600/424 |
| 6,014,579 | * | 1/2000 | Pomeranz et al. .................. 600/374 |

FOREIGN PATENT DOCUMENTS 0 835 634 A1  4/1998  (EP) .
WO 94/06349   3/1994  (WO) .

OTHER PUBLICATIONS

Gepstein et al., "A Novel Method for Nonfluoroscopic Catheter–Based Electroanatomical Mapping of the Heart", *Circulation*, 95(6) :1611–1622 (Mar. 18, 1997).

Meyer et al., "Application of Sonomicrometery andMulti-dimensional Scaling to Cardiac Catheter Tracking", *Transactions on Biomedical Engineering* 44(11) :1061–1067 (Nov. 1997).

* cited by examiner

*Primary Examiner*—John P. Lacyk
*Assistant Examiner*—Brian Szmal
(74) *Attorney, Agent, or Firm*—Dorsey & Whitney LLP

(57) ABSTRACT

A device for locating an electrode used in endocardial treatment comprises further electrode means to be positioned inside the heart together with the electrode, the further electrode means being able to adopt a geometrical arrangement defining a system of spatial coordinates. Polarization means are provided for applying respective electrical signals to at least one of the electrode and the further electrode means, as well as detector means connected to the electrode and to the further electrode means for detecting the potential established between the electrode and the further electrode means as a result of the application of the electrical signals. Measuring means sensitive to the potential are capable of determining, on the basis of the potential, the position of the electrode relative to the system of spatial coordinates defined by the further electrode means.

25 Claims, 2 Drawing Sheets

DEVICE FOR LOCATING ENDOCARDIAL ELECTRODES

RELATED APPLICATION

Figure 1:
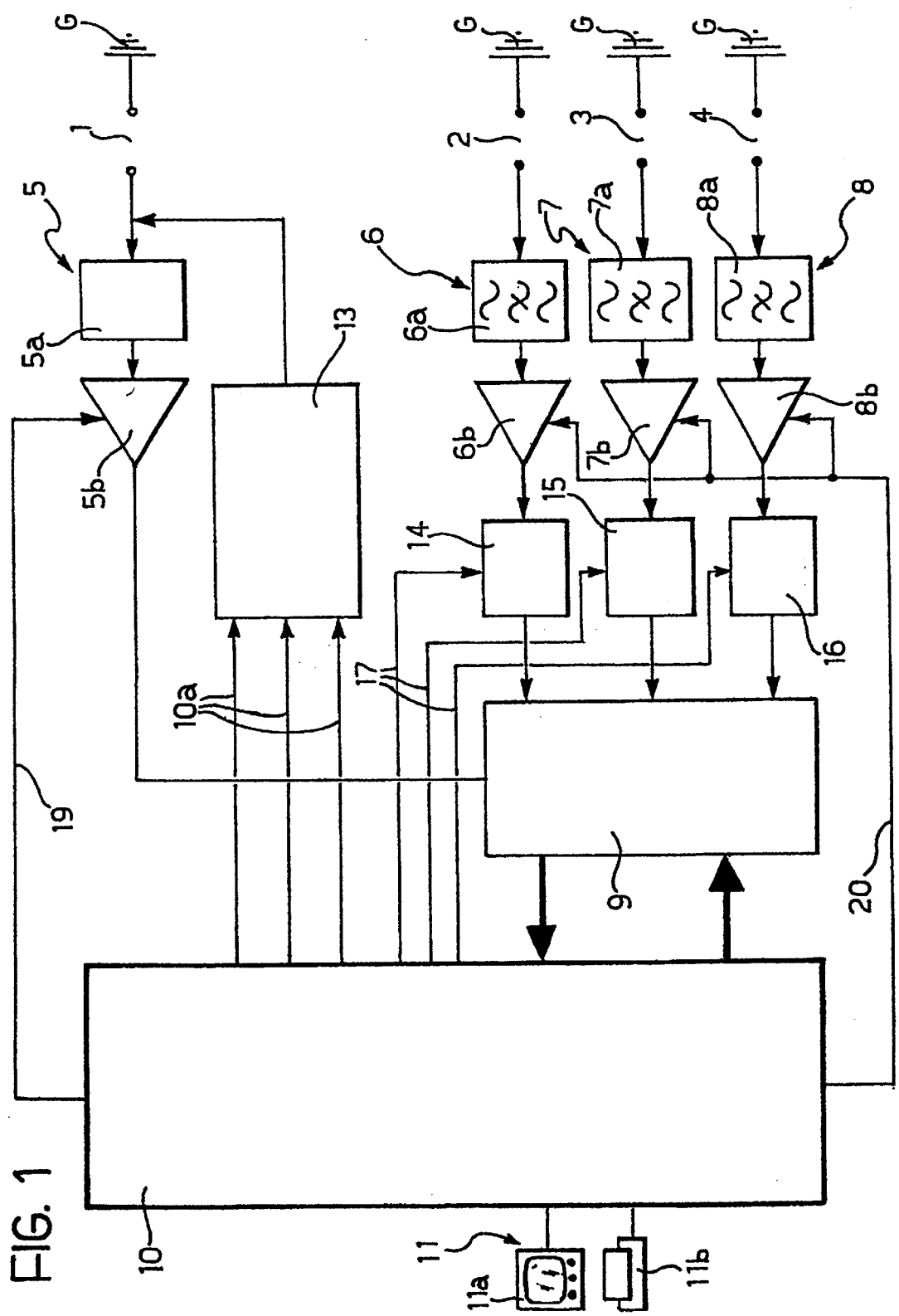

This application claims priority to European Patent Application No. 99830032.1, filed on Jan. 28, 1999, the entire teachings of which are incorporated herein by reference.

The present invention relates in general to techniques for operating on the heart which are performed transvenously with the use of catheters.

During these transvenous heart procedures performed with the use of catheters, it is very important to be able to locate the pole of the catheter used—generally within a three-dimensional space. This need is very marked in radio-frequency ablation and electro-physiological mapping procedures which require so-called "navigation" of the catheter along a complex endocardial surface.

Recently, non-fluoroscopic locating systems based on magnetic systems for mapping the catheter-pole position have been proposed. Devices of this type have been used in the electro-physiological mapping of the endocardium with simultaneous recording of the pole position and of the electrogram. In this connection, the work "A novel method for nonfluoroscopic catheter-based electroanatomical mapping of the heart" by L. Gepstem, G. Hayam and S. A. Ben-Haim in Circ., Vol. 95, No. 6, Pages 1611–1622, 1977 may usefully be consulted.

The device concerned has been clinically evaluated and has demonstrated its usefulness in reducing exposure to X-rays so that it is possible to return to a specific anatomical site of interest.

A system based on sonomicrometry recently proposed for the same purpose consists of a scanning catheter fitted with a piezoelectric transducer which can send ultrasound pulses to seven reference sensors fitted on the epicardial surface of a sheep's heart. In this connection, the work "Application of sonomicrometry and multidimensional scaling to cardiac catheter tracking" by Scott A. Meyer and Patrick D. Wolf in IEEE transactions on Biomedical Engineering, Vol. 44, No. 11 November 1997 may usefully be consulted.

The present invention fits into this line of research which is directed towards locating the pole of a catheter operating in an endocardial site whilst avoiding fluoroscopic location.

According to the present invention, this object is achieved by means of a device having the characteristics recited specifically in the following claims.

Briefly, the solution according to the invention is based— in the currently preferred embodiment—on the principle of the vectorial de-composition of an electric field onto three axes, the electric field being generated by pulses below the stimulation threshold, delivered to the endocardial surface by the pole of a scanning catheter.

The device according to the invention, which is intended preferably for temporary use in acute situations, preferably comprises a four-pole, triaxial geometric reference system, associated with a lead having at least one core for scanning the endocardial surface, as well as an external unit for processing data in real time. The device, again preferably, is for use in combination with a pulse generator for generating direct-current pulses of programmable frequency and duration, and with a system for displaying and printing maps of the endocardial surface or of the physiological signals detected thereon.

Again in the currently-preferred embodiment, the system is based upon the detection, within a heart chamber, of the vectorial projections, onto a triaxial spatial reference system, of the electrical potential generated between a pole or electrode of a scanning lead (which is positioned at different sites of the endocardium by the operator) and a central pole acting as an origin of the triaxial reference system. The reference lead is also positioned inside the same heart chamber or in any case in a position such as to lead to little distortion of the electric field between the reference lead and the scanning pole.

The external data-processing unit analyzes the three vectorial components of the potential. This is done with reference to the inclination of the axes which, although they are fixed, are not necessarily perpendicular. The relative position of the scanning pole, which is guided by the operator so as to describe the endocardial surface under investigation, can thus be calculated by a suitable algorithm.

External electrical stimulation or electrotonic inhibition devices and/or devices for measuring electro-physiological quantities may optionally be connected to the scanning pole, enabling the respective data to be transmitted to the processing unit, possibly for association with the respective spatial position. This enables three-dimensional maps or two-dimensional developments of the parameter investigated to be displayed.

Whilst keeping the reference lead in situ, it is possible to replace the scanning lead with a lead of a different type, for example, having radio-frequency ablation electrodes, optical fibres for endoscopy and/or for topical application of radiation, or devices for performing microscopic surgical operations. Such a lead may nevertheless have a conductive pole with the same characteristics as the previous scanning lead to enable the lead to be positioned and a display to be provided on the previously-constructed map, by similar methods.

In order to be able to insert the reference system with its three axes and the respective poles in the blood vessel, it is possible to use, for example, two coaxial leads of which the outer one has the function of a movable sheath with facilitated relative sliding.

This facilitates transvenous insertion into the heart chamber under investigation and the subsequent opening-out in situ of a reference system having intrinsic mechanical stability. This stability can also be achieved actively, for example, by associating with each of the axes respective pole tubules made of a material and by techniques similar to those used for balloon catheters for angioplasty treatments (PTCA). These soft tubules can easily be housed inside a retractable sheath and can subsequently become stiff after being pressurized by a suitable gas or liquid. The reverse operation enables the reference lead to be recovered in each of the systems described.

Although the currently preferred embodiment provides for the production of a three-dimensional positioning system, the invention may also be implemented—in simplified versions—by means of two-dimensional reference systems or, potentially, even one-dimensional systems. Naturally, in this case, the greater ease of implementation compensates for the reduced richness of the data.

In this connection, it is again pointed out that the reference system does not necessarily have to be a perpendicular Cartesian system. Three-dimensional reference systems of different types, for example polar or cylindrical systems, may in fact be used within the scope of the invention.

Figure 2:
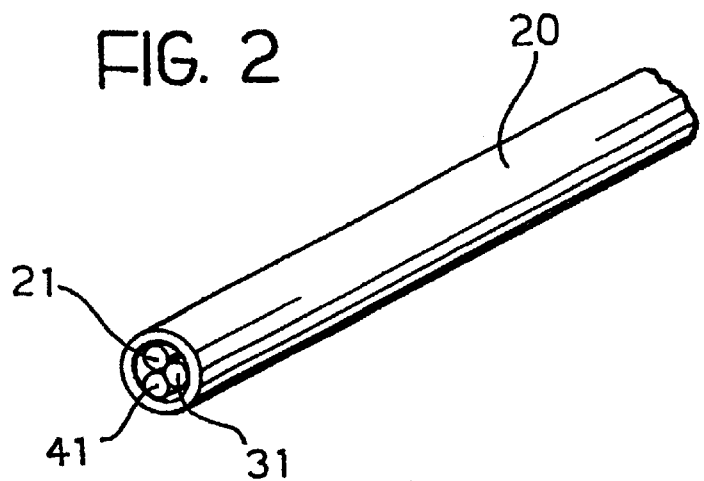
Figure 3:
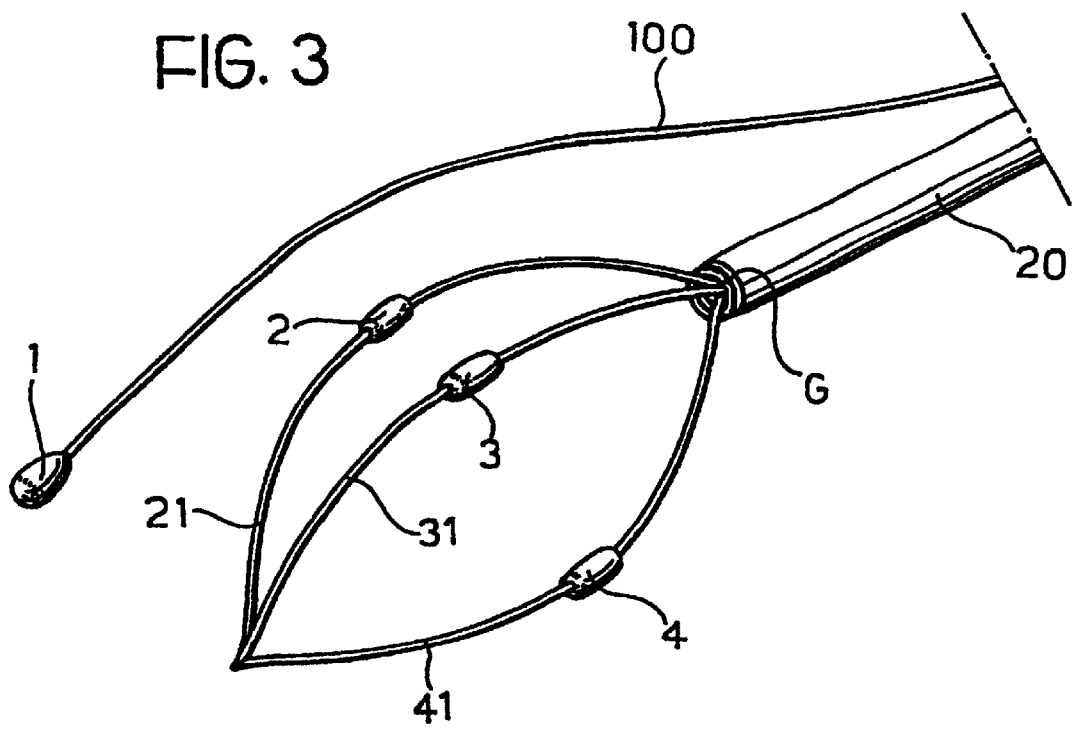

The invention will now be described, purely by way of non-limiting example, with reference to the appended drawings, in which:

FIG. 1 shows the structure of a device according to the invention as a whole, in the form of a block diagram, and FIGS. 2 and 3 show the part of the device according to the invention which is intended to be introduced into the endocardial site, in the contracted, insertion configuration and in the opened-out, operative position, respectively.

In FIG. 1, four electrodes or poles which can be introduced into the endocardial region in an arrangement such as that shown in FIGS. 2 and 3 below, are indicated 1, 2, 3 and 4.

All four of the electrodes in question (which are formed in accordance with techniques known in the field of endocardial electrical treatment and do not therefore require detailed description herein) are electrically conductive in the sense that they have at least one electrically-conductive portion (pole). This pole is connected to a corresponding polarization conductor or line which extends from the electrode towards the other components of the device shown in FIG. 1 which are usually situated in a region outside the body. This enables the electrodes 1 to 4 to be brought to respective predetermined potential levels and/or enables their relative positions and, in particular, the position of the electrode 1 relative to the other electrodes 2, 3 and 4 constituting the reference system, to be assessed by means of any variations of the aforementioned relative potentials (in practice, the potential differences existing between the electrode 1 and the other electrodes 2, 3 and 4).

The "metrics" of the respective space can be established clearly from the respective potentials detected between the electrodes 2, 3 and 4, which act as reference elements, since the relative positions, which can be established, for example, by providing for a predetermined opened-out geometrical arrangement (see, for example, FIG. 3), are known.

Once these metrics have been established, the problem of locating the electrode 1 can be brought down to the geometrical problem (the solution of which is known, irrespective of the type of reference system) of determining the coordinates of a point relative to a three-dimensional reference system (for example, a perpendicular Cartesian system), the distance of the electrode from each of the reference electrodes (which can be inferred from the respective potential difference) being known.

As already stated, the reference to a perpendicular Cartesian system is mainly theoretical. In most cases, the three reference electrodes 2, 3 and 4 do not precisely define a geometrical arrangement of this type. Any multidimensional reference system (and the coordinates of a point in the system) can nevertheless be brought back to a perpendicular Cartesian reference system and to the coordinates thereof by algorithmic means.

As already stated in the introductory part of this description, the electrode 1 (which is generally identified as the "scanning" electrode) can in fact adopt very different functional characteristics in dependence on the specific requirements of the endocardial treatment to be performed.

Respective units for processing/conditioning the signals coming from the various electrodes 1 to 4 are indicated 5 to 8 and each comprises, in the currently preferred embodiment, a filter 5a–8a having the main function of rejecting noise and interference, and an amplifier unit 5b–8b.

Upon the assumption that the electrode 1 concerned has the predominant function of scanning the myocardial wall, the signal output by the respective amplifier 5b constitutes a set of endocardial scanning signals to be sent to an analog/digital conversion circuit 9 in dependence on subsequent processing by a timing and algorithmic processing unit 10.

This latter unit comprises basically:

a portion (of generally known type) which provides for the processing of the signals coming from the electrode 1, and another portion, the function of which is basically to derive by algorithmic means (by solving the known geometrical problem stated above) the position of the electrode 1 relative to the reference system defined by the electrodes 2 to 4, for subsequent display, for example, on one or more display units 11.

The latter may advantageously be constituted by a video unit 11a (for displaying visual data in real time) and/or by a printer 11b (for generating graphical information), the information being inherent in the data resulting from the endocardial scanning.

The unit 10 also sends control signals (of generally known type and usually relating to an initiation or trigger signal, to amplitude and to width) towards a signal generator unit 13 (of known type, which may vary according to the nature of the electrode 1), on one or more lines, generally indicated 10a.

The signals produced by the unit 13 are intended to be sent to the electrode 1 through the catheter which connects the electrode 1 to the portions of the device which are located outside the body.

For the purpose of implementing the present invention, the signals in question are preferably constituted by sub-threshold stimulation signals (which are thus not able to induce undesired contraction of the heart muscle) which can be "picked up" by the reference leads 2 to 4. The respective signals picked up are passed through the filter and amplification units 6 to 8 and are transferred, preferably via respective sample-and-hold units, indicated 14 to 16, to the conversion unit 10 for transfer to the processing unit 11.

The lines generally indicated 17 identify lines by means of which the unit 10 transfers to the units 14 to 16 signals for driving the sampling function relating to each of the reference electrodes 2 to 4.

Finally, the unit 10 transfers respective gain-control signals (in known manner), by means of respective lines indicated 19 and 20, to the amplifier 5b associated with the electrode 1 so as to perform the automatic gain-control function (known per se), as well as to the amplifiers 6b–8b. In this case, the signals transmitted are signals relating to the gains of the test pulses.

FIGS. 2 and 3 show the probe portion of the device according to the invention; in practice this is the head comprising the electrodes 2 to 4 which are intended to be inserted into one of the heart chambers by catheterization so that the scanning electrode 1, which is also inserted in the corresponding chamber by catheterization, can be located. The probe portion carrying the electrodes 2 to 4 is shown in the contracted, insertion position (FIG. 2) and in the opened-out or unfolded position of use (FIG. 3) in which the electrodes have been brought to the spread-out position by respective support elements 21, 31, and 41 of known type made, for example, of a material with a shape memory.

FIG. 2 shows the unit used for catheterization. This unit comprises, basically, a sheath 20 which can be retracted onto the body of the insertion catheter (which is not shown in detail but is of known type) as shown in FIG. 3 in order to achieve a dual effect of uncovering and releasing the elements 21, 31 and 41.

The three electrodes 2, 3 and 4, open out so as to be arranged in a spread-out configuration; they can thus constitute, in accordance with the criteria described above, the three axes of a reference system usable to identify and/or to display externally the position of the lead 1. In the proximal or root portion of the elements 21, 31, and 41, there is preferably at least one further reference electrode G, to which the potentials of the electrodes 2, 3 and 4 are in fact related, as is also that of the electrode 1, with regard to the determination of the potential established between the electrodes. In the electrical diagram of FIG. 1, this reference electrode is in fact identified by the earth or ground of the circuit.

In particular, it has been found preferable to arrange for the position of the electrode 1 to be detected by generating the respective signals in synchronism with the heart movement (deduced, for example, from an external electrocardiographic signal) so as to perform the detection in successive heart cycles, with the benefit of a substantially identical position of the heart muscle in the successive cycles. The necessary synchronization in order for the function of locating the electrode 1 to be performed at a predetermined stage (for example, the stage of maximum fullness, that is, the end of the diastole, or the stage of maximum emptiness, that is, the end of the systole) of the heart cycle can easily be performed by means of the unit 10.

Naturally, the principle of the invention remaining the same, the details of construction and forms of embodiment may be varied widely with respect to those described and illustrated, without thereby departing from the scope of the present invention as claimed in the following claims.

What is claimed is:

1. A device for locating an electrode used in endocardial treatment, comprising:
    a first electrode means for contacting an endocardial surface;
    a further electrode means for adopting a geometric arrangement defining a triaxial system of spatial coordinates which is positioned inside the endocardial surface without enclosing the first electrode means;
    a polarization means for applying respective electrical signals to at least one of the electrode and the further electrode means;
    a detector means connected to the first electrode means and to the further electrode means for detecting the potential established between the first electrode means and the further electrode means as a result of the application of the electrical signals; and
    a measuring means sensitive to the potential and capable of determining, on the basis of the potential, the position of the first electrode means relative to the system of spatial coordinates defined by the further electrode means such that a characteristic of the endocardial surface can be electronically formed from a sequence of position measurements with the first electrode means contacting the endocardial surface.

2. The device of claim 1, wherein the further electrode means comprise a plurality of electrodes which can extend in different directions so that each of the electrodes of the plurality identifies at least one respective component of the triaxial system of spatial coordinates.

3. The device of claim 2, wherein the plurality comprises three electrodes.

4. The device of claim 1, wherein the polarization means generate the electrical signals as electrical signals the intensity of which is below the heart-muscle stimulation threshold.

5. The device of claim 1, wherein the electrical signals are pulsed signals.

6. The device of claim 5, wherein the polarization means can vary at least one of the parameters constituted by pulse amplitude and pulse width.

7. The device of claim 1, wherein the first electrode means has associated endocardial operating means selected from the group consisting of:
    ablation electrodes;
    optical fibres for endoscopy;
    optical fibres for the topical application of laser radiation; and devices for performing microscopic surgical operations.

8. The device of claim 1, wherein the further electrode means have associated restraining means for holding the further electrode means in a contracted position during insertion into a heart chamber, the restraining means being releasable from the further electrode means at least locally so as to allow the further electrode means to open out to the geometrical arrangement defining the system of spatial coordinates.

9. The device of claim 8, wherein the restraining means comprise a sheath which restrains the further electrode means in the contracted position and which can be retracted so as to allow the further electrode means to open out.

10. The device of claim 1, comprising positive erection means associated with the further electrode means, the erection means being capable of being activated selectively in order to open out the further electrode means to the geometrical arrangement defining the geometrical system of spatial coordinates.

11. The device of claim 1, comprising means for synchronization with an external electrocardiographic signal in order to determine the position of the first electrode means relative to the system of spatial coordinates at a predetermined stage of successive heart cycles.

12. A device for locating a moveable electrode used in endocardial treatment, comprising:
    a moveable electrode that can be positioned to contact a plurality of locations on an endocardial surface;
    a positioning electrode defining a triaxial system of spatial coordinates, the positioning electrode capable of being positioned inside a subject's heart without enclosing the moveable electrode;
    a polarization circuit that applies an electrical signal to the moveable electrode and the positioning electrode;
    a detector connected to the moveable electrode and to the positioning electrode that detects a potential established between the moveable and the positioning electrode as a result of the application of the electrical signal; and
    a measuring circuit sensitive to the potential, the measuring circuit determining, on the basis of the detected potential, a position of the moveable electrode relative to the system of spatial coordinates defined by the positioning electrode such that a characteristic of the endocardial surface can be electronically formed from a sequence of position measurements with the moveable electrode contacting the endocardial surface at a plurality of locations.

13. The device of claim 12 wherein the positioning electrode comprises a plurality of positioning electrodes, each positioning electrode defining a spatial coordinate of the system of coordinates.

14. The device of claim 12 further comprising a generator connected to the moveable electrode, an analog to digital conversion circuit connected to the positioning electrode and the moveable electrode, and a processor connected to the conversion circuit.

15. A method of locating a probe electrode comprising:
    providing a probe assembly including a positioning electrode array defining a geometric body;

contacting a tissue surface at a first location with a probe comprising a probe body and a probe electrode;

inserting the probe assembly into a body;

deploying the positioning electrode array within the body such that the probe is located outside the geometric body;

applying an electrical signal to the probe electrode and the positioning electrode;

detecting a positioning signal in response to the applied signal;

determining a position of the probe electrode with the positioning signal; and repositioning the probe electrode to contact the tissue surface at a second location and repeating the applying, detecting and determining steps to generate an electronic representation of the tissue surface.

16. The method of claim 15 further comprising providing a catheter for insertion in a body lumen, and inserting the probe assembly into the body through the catheter.

17. The method of claim 15 wherein the geometric body defines a three-dimensional coordinate system.

18. The method of claim 15 further comprising positioning the probe assembly within a heart for treatment or examination of endocardial tissue.

19. The method of claim 15 further comprising providing a sheath that restrains the positioning electrode array in a delivery position such that relative movement between the sheath and the positioning electrode array provides for expansion of the positioning electrode to a measurement position.

20. The method of claim 19 wherein the positioning electrode array comprises a plurality of positioning electrodes, each mounted to a shape memory material that expands to the measurement position when translated longitudinally relative to the sheath.

21. The method of claim 15 further comprising forming a map of the tissue surface.

22. The method of claim 15 further comprising:

measuring a physiological signal at the first location; and measuring a physiological signal at the second location.

23. The method of claim 15 further comprising providing a pulse generator that generates a direct current (DC) pulse having a programmable frequency.

24. The method of claim 15 further comprising providing a data processor connected to the probe electrode and the positioning electrode array, the data processor controlling a pulse generator such that the probe electrode emits a sub-threshold signal into tissue without inducing muscle contraction.

25. The method of claim 24 further comprising synchronizing the emission of probe electrode signals with a heart movement cycle.

* * * * *